(12) United States Patent
Sloan et al.

(10) Patent No.: US 8,383,036 B2
(45) Date of Patent: *Feb. 26, 2013

(54) METHODS FOR NEUTRALIZING ANTHRAX OR ANTHRAX SPORES

(75) Inventors: Mark A. Sloan, Spring Branch, TX (US); Jeevalatha Vivekananda, San Antonio, TX (US); Eric A. Holwitt, San Antonio, TX (US); Johnathan L. Kiel, Universal City, TX (US)

(73) Assignee: Conceptual Mindworks, Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/973,681

(22) Filed: Dec. 20, 2010

(65) Prior Publication Data

US 2012/0134877 A1 May 31, 2012

Related U.S. Application Data

(60) Division of application No. 10/291,336, filed on Nov. 8, 2002, now Pat. No. 7,892,484, which is a continuation-in-part of application No. 09/978,753, filed on Oct. 15, 2001, now Pat. No. 6,569,630, which is a continuation-in-part of application No. 09/608,706, filed on Jun. 30, 2000, now Pat. No. 6,303,316.

(60) Provisional application No. 60/360,844, filed on Feb. 28, 2002, provisional application No. 60/333,085, filed on Nov. 13, 2001.

(51) Int. Cl.
*A61L 2/00* (2006.01)

(52) U.S. Cl. ................................ 422/20; 422/21; 422/22

(58) Field of Classification Search .................... 422/20, 422/21, 22
See application file for complete search history.

(56) References Cited

U.S. PATENT DOCUMENTS 5,270,163 A * 12/1993 Gold et al. .................... 435/6.11
6,737,236 B1 * 5/2004 Pieken et al. ..................... 435/5

OTHER PUBLICATIONS

Wainwright (1998) J. Antimicrobial Chemotherapy 42:13-28.*
Bruno and Kiel (1999) Biosensors & Bioelectronics 14:457-464 (available online on Jun. 28, 1999).*
Bruno and Kiel (1993) Electricity and Magnetism in Biology and Medicine (San Francisco Press, Inc.), pp. 231-233.*

* cited by examiner

*Primary Examiner* — Jon E Angell
(74) *Attorney, Agent, or Firm* — Faegre Baker Daniels LLP

(57) ABSTRACT

The present invention concerns methods, compositions and apparatus for neutralizing bioagents, wherein bioagents comprise biowarfare agents, biohazardous agents, biological agents and/or infectious agents. The methods comprise exposing the bioagent to an organic semiconductor and exposing the bioagent and organic semiconductor to a source of energy. Although any source of energy is contemplated, in some embodiments the energy comprises visible light, ultraviolet, infrared, radiofrequency, microwave, laser radiation, pulsed corona discharge or electron beam radiation. Exemplary organic semiconductors include DAT and DALM. In certain embodiments, the organic semiconductor may be attached to one or more binding moieties, such as an antibody, antibody fragment, or nucleic acid ligand. Preferably, the binding moiety has a binding affinity for one or more bioagents to be neutralized. Other embodiments concern an apparatus comprising an organic semiconductor and an energy source. In preferred embodiments, the methods, compositions and apparatus are used for neutralizing anthrax spores.

14 Claims, 3 Drawing Sheets

CONTROL SPORE

FIG. 1A

HPM EXPOSED WITH DALM

Shot # 106
PCR % Kill of B.a. Spores
vs B.a. Spores + DALM

- Spores only
- Spores + DALM

FIG. 3

METHODS FOR NEUTRALIZING ANTHRAX OR ANTHRAX SPORES

CROSS-REFERENCE TO RELATED APPLICATION

This application is a divisional of, and claims priority to U.S. patent application Ser. No. 10/291,336 filed Nov. 8, 2002, which claims the benefit under 35 U.S.C. §119(e) of provisional Patent Application Ser. No. 60/333,085, filed Nov. 13, 2001 and 60/360,844, filed Feb. 28, 2002. U.S. patent application Ser. No. 10/291,336 is a continuation-in-part of U.S. patent application Ser. No. 09/978,753 (now issued U.S. Pat. No. 6,569,630) filed Oct. 15, 2001, which was a continuation-in-part of U.S. patent application Ser. No. 09/608,706 (now issued U.S. Pat. No. 6,303,316), filed Jun. 30, 2000. The entire texts of these applications are incorporated herein by reference in their entirety for all purposes.

The invention described herein was made with Government support under contracts F41622-96-D-008 and F41824-00-D-700 awarded by the Department of the Air Force and Department of Energy contract number DE-AC06-76RL01830. The Federal Government has a nonexclusive, nontransferable, irrevocable, paid-up license to practice or have practiced for or on behalf of the United States the subject invention.

FIELD OF INVENTION

The present invention relates to the field of biowarfare, biohazards and infectious agents. More particularly, the present invention relates to methods, apparatus and compositions for neutralizing biowarfare agents, biohazardous agents and/or infectious agents.

DESCRIPTION OF RELATED ART

There is a great need for effective methods and apparatus for neutralizing biological warfare agents, biohazardous agents, and/or infectious agents (hereafter, collectively referred to as "bioagents"). In particular, there is a great need for effective methods and apparatus for neutralizing *Bacillus anthracis* spores and other bioagents used in biological warfare.

Anthrax spores are among the most difficult bioagents to eradicate. Starting in the 1940s, the British government treated anthrax contamination of Guinard Island, a biological warfare test site, with 280 tons of formaldehyde over a 36 year period in order to decontaminate the site.

Present methods of anthrax spore neutralization are impractical in the contexts of mail delivery systems and decontamination of public areas. These include use of pressurized steam at elevated temperatures or topical treatment with highly caustic concentrated sodium hypochlorite solutions or with certain disinfecting foam products. None of these could be used to decontaminate, for example, letter mail without destroying it.

More recently, electron beam or electron accelerator technologies have been applied to bacterial neutralization. High doses of irradiation were required in order to inactivate anthrax spores. The technology is expensive and not readily adaptable to portable systems that could be easily deployed in the field. The energy levels required for decontamination also occasionally cause combustion or other destruction of the decontaminated material.

Thus, there is a need for a method to identify and neutralize bioagents in general, without substantial adverse impact on the contaminated object or the environment. There is a specific need for a portable, cost-effective apparatus, compositions and methods for neutralizing *Bacillus anthracis* spores.

SUMMARY OF THE INVENTION

The present invention fulfills an unresolved need in the art by providing apparatus, compositions and methods for neutralizing bioagents. In certain embodiments, compositions comprising an organic semiconductor may be applied to a bioagent. The organic semiconductor may be used as a molecular transducer, absorbing various forms of radiation or other types of energy, such as plasma, transmitting the energy to bioagents and inactivating them. In various embodiments, organic semiconductors of use may include polydiazoaminotyrosine (DAT), diazoaluminomelanin (DALM) and/or other known organic semiconductors. Forms of energy of potential use include microwaves, visible light, ultraviolet, infrared, radiofrequency irradiation and/or pulsed corona (plasma) discharge. In specific embodiments, the apparatus used to provide pulsed corona discharge may be a pulsed corona reactor (Titan Pulse Sciences Division, San Leandro, Calif.).

In alternative embodiments, neutralization of bioagents may be facilitated by attaching the organic semiconductor to one or more binding moieties. Binding moieties of use may include, without limitation, nucleic acid ligands, proteins, peptides, receptor proteins, antibodies and or antibody fragments, as well as modified forms of each. Attachment of the organic semiconductor to the binding moiety may be either covalent or noncovalent. The binding moiety preferably binds selectively or specifically to the bioagent to be neutralized. Attachment of organic semiconductor to binding moiety provides for a more selective and/or specific neutralization of the bioagent. In certain embodiments, the binding moiety itself may facilitate energy transfer from the organic semiconductor to the bioagent. Alternatively, the binding moiety may provide for a closer physical proximity of organic semiconductor and bioagent, thereby increasing the effectiveness of neutralization. In certain embodiments, the binding moiety may comprise part or all of the sequence of SEQ ID NO:4, SEQ ID NO:5 and/or SEQ ID NO:6.

Various embodiments concern methods of bioagent neutralization, comprising exposing a bioagent to an organic semiconductor and activating the organic semiconductor. Activation may utilize various forms of radiation or energy, as discussed above. Further embodiments may comprise attaching the organic semiconductor to one or more binding moieties. The binding moieties preferably exhibit selectivity or specificity for one or more bioagents of interest. In preferred embodiments, the bioagent comprises *Bacillus anthracis* spores.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 shows the destruction of anthrax spores using an organic semiconductor and a high power microwave pulse. Conditions were as described in Example 1. (A) Control spore exposed to HPM alone. (B) Anthrax spore exposed to HPM in the presence of DALM.

FIG. 2 shows the destruction of anthrax spores exposed to an organic semiconductor and pulsed corona discharge. Conditions were as described in Example 2.

FIG. 3 shows a replicate of the assay performed in FIG. 2.

DESCRIPTION OF ILLUSTRATIVE EMBODIMENTS

Definitions

As used herein, "a" or "an" may mean one or more than one of an item.

The term "bioagent" encompasses biowarfare agents, biohazardous agents, biological agents, and/or infectious agents. In preferred embodiments, a "bioagent" is one that is capable of causing a disease state or any other pathological or toxicological condition or effect in a host exposed to the bioagent, including the death of the host. Hosts include but are not limited to mammalian hosts, such as humans or animals. "Bioagents" include, but are not limited to, bacteria, spores, anthrax spores, viruses, protozoans, parasites, fungi, yeast, mold, algae, amoebae, microbes, toxins, prions, microorganisms and pathogenic, nonpathogenic or saprophytic microbes.

Non-limiting examples of bioagents within the scope of the present invention include those listed in Table 1.

TABLE 1

Exemplary Bioagents

| | |
|---|---|
| Actinobacillus spp. | Bacteroides spp. |
| Actinomyces spp. | Balantidium coli |
| Adenovirus (types 1, 2, 3, 4, 5 et 7) | Bartonella bacilliformis |
| Adenovirus (types 40 and 41) | Blastomyces dermatitidis |
| Aerococcus spp. | Bluetongue virus |
| Aeromonas hydrophila | Bordetella bronchiseptica |
| Ancylostoma duodenale | Bordetella pertussis |
| Angiostrongylus cantonensis | Borrelia burgdorferi |
| Ascaris lumbricoides | Branhamella catarrhalis |
| Ascaris spp. | Brucella spp. |
| Aspergillus spp. | B. abortus |
| Bacillus anthracis | B. canis, |
| Bacillus cereus | B. melitensis |
| B. suis | Diphtheroids |
| Brugia spp. | Eastern (Western) equine encephalitis virus |
| Burkholderia mallei | |
| Burkholderia pseudomallei | Ebola virus |
| Campylobacter fetus subsp. fetus | Echinococcus granulosus |
| Campylobacter jejuni | Echinococcus multilocularis |
| C. coli | Echovirus |
| C. fetus subsp. jejuni | Edwardsiella tarda |
| Candida albicans | Entamoeba histolytica |
| Capnocytophaga spp. | Enterobacter spp. |
| Chlamydia psittaci | Enterovirus 70 |
| Chlamydia trachomatis | Epidermophyton floccosum, Microsporum spp. Trichophyton spp. |
| Citrobacter spp. | |
| Clonorchis sinensis | Epstein-Barr virus |
| Clostridium botulinum | Escherichia coli, enterohemorrhagic |
| Clostridium difficile | Escherichia coli, Enteroinvasive |
| Clostridium perfringens | Escherichia coli, Enteropathogenic |
| Clostridium tetani | Escherichia coli, enterotoxigenic |
| Clostridium spp. | Fasciola hepatica |
| Coccidioides immitis | Francisella tularensis |
| Colorado tick fever virus | Fusobacterium spp. |
| Corynebacterium diphtheriae | Gemella haemolysans |
| Coxiella burnetii | Giardia lamblia |
| Coxsackievirus | Giardia spp. |
| Creutzfeldt-Jakob bioagent, Kuru | Haemophilus ducreyi |

TABLE 1-continued

Exemplary Bioagents

| | |
|---|---|
| bioagent | Haemophilus influenzae (group b) |
| Crimean-Congo hemorrhagic fever virus | Hantavirus |
| Cryptococcus neoformans | Hepatitis A virus |
| Cryptosporidium parvum | Hepatitis B virus |
| Cytomegalovirus | Hepatitis C virus |
| Dengue virus (1, 2, 3, 4) | Hepatitis D virus |
| Hepatitis E virus | Neisseria meningitides |
| Herpes simplex virus | Neisseria spp. |
| Herpesvirus simiae | Nocardia spp. |
| Histoplasma capsulatum | Norwalk virus |
| Human coronavirus | Omsk hemorrhagic fever virus |
| Human immunodeficiency virus | Onchocerca volvulus |
| Human papillomavirus | Opisthorchis spp. |
| Human rotavirus | Parvovirus B19 |
| Human T-lymphotrophic virus | Pasteurella spp. |
| Influenza virus | Peptococcus spp. |
| Junin virus/Machupo virus | Peptostreptococcus spp. |
| Klebsiella spp. | Plesiomonas shigelloides |
| Kyasanur Forest disease virus | Powassan encephalitis virus |
| Lactobacillus spp. | Proteus spp. |
| Legionella pneumophila | Pseudomonas spp. |
| Leishmania spp. | Rabies virus |
| Leptospira interrogans | Respiratory syncytial virus |
| Listeria monocytogenes | Rhinovirus |
| Lymphocytic choriomeningitis virus | Rickettsia akari |
| Marburg virus | Rickettsia prowazekii, R. Canada |
| Measles virus | Rickettsia rickettsii |
| Micrococcus spp. | Ross river virus/ O'Nyong-Nyong virus |
| Moraxella spp. | Rubella virus |
| Mycobacterium spp. | Salmonella choleraesuis |
| Mycobacterium tuberculosis, M. bovis | Salmonella paratyphi |
| Mycoplasma hominis, M orale, M salivarium, M fermentans | Salmonella typhi |
| | Salmonella spp. |
| Mycoplasma pneumoniae | Schistosoma spp. |
| Naegleria fowleri | Scrapie bioagent |
| Necator americanus | Serratia spp. |
| Neisseria gonorrhoeae | Shigella spp. |
| Sindbis virus | Yersinia pestis |
| Sporothrix schenckii | |
| St. Louis encephalitis virus | |
| Murray Valley encephalitis virus | |
| Staphylococcus aureus | |
| Streptobacillus moniliformis | |
| Streptococcus agalactiae | |
| Streptococcus faecalis | |
| Streptococcus pneumoniae | |
| Streptococcus pyogenes | |
| Streptococcus salivarius | |
| Taenia saginata | |
| Taenia solium | |
| Toxocara canis, T. cati | |
| Toxoplasma gondii | |
| Treponema pallidum | |
| Trichinella spp. | |
| Trichomonas vaginalis | |
| Trichuris trichiura | |
| Trypanosoma brucei | |
| Ureaplasma urealyticum | |
| Vaccinia virus | |
| Varicella-zoster virus | |
| Venezuelan equine encephalitis | |
| Vesicular stomatitis virus | |
| Vibrio cholerae, serovar 01 | |
| Vibrio parahaemolyticus | |
| Wuchereria bancrofti | |
| Yellow fever virus | |
| Yersinia enterocolitica | |
| Yersinia pseudotuberculosis | |

"Neutralize" as used herein means to destroy, kill, inhibit or inactivate a bioagent. In preferred embodiments, a neutralized bioagent is one that is no longer capable of causing a disease state or any other pathological or toxicological condition or effect, such as infection or death, in a host exposed to the bioagent. In more preferred embodiments, a neutralized bioagent is dead. However, it is contemplated within the scope of the invention that neutralization may be only partially effective. For example, a neutralized bioagent may cause a less severe disease state or condition in a host, compared to a non-neutralized bioagent. Alternatively, a neutralized bioagent may be capable of infecting a smaller percentage of a population exposed to the bioagent, or may be capable of infecting a host under more limiting conditions, such as exposure at higher dosages, than a non-neutralized bioagent.

"Organic semiconductor" means a conjugated (alternating double and single bonded) organic compound in which regions of electrons and the absence of electrons (holes or positive charges) can move with varying degrees of difficulty through the aligned conjugated system (varying from insulator to conductor). An organic semiconductor may be thought of as the organic equivalent of a metal, in terms of electrical properties. Organic semiconductors are distinguished from metals in their spectroscopic properties. Organic semiconductors may be fluorescent, luminescent, chemiluminescent, sonochemiluminescent, thermochemiluminescent or electrochemiluminescent (Bruno et al., 1998) or may be otherwise characterized by their absorption, reflection or emission of electromagnetic radiation, including infrared, ultraviolet or visible light. In certain embodiments, organic semiconductors may be considered as molecular transducers that are capable of absorbing one form of energy and converting it into another form of energy. In a preferred embodiment, an activated organic semiconductor is utilized to neutralize a bioagent. Non-limiting examples of organic semiconductors include DAT and/or DALM.

"Binding moiety" refers to a molecule or aggregate of molecules that has a binding affinity for one or more bioagents. The term is not limiting as to the type of molecule or aggregate. Non-limiting examples of binding moieties include peptides, polypeptides, proteins, glycoproteins, antibodies, antibody fragments, antibody derivatives, receptors, enzymes, transporters, binding proteins, cytokines, hormones, substrates, substrate analogs, metabolites, inhibitors, activators, biotin-avidin, lipids, glycolipids, carbohydrates, polysaccharides, nucleic acids, nucleic acid ligands, polynucleotides and oligonucleotides, as well as chemically modified forms of each.

"Nucleic acid ligand" means a non-naturally occurring nucleic acid having a desirable action on a bioagent. A desirable action includes, but is not limited to, binding to the bioagent, catalytically changing the bioagent, reacting with the bioagent in a way that modifies or alters the bioagent or the functional activity of the bioagent, covalently attaching to the bioagent, facilitating the reaction between the bioagent and another molecule such as an organic semiconductor, and neutralizing the bioagent.

DAT

In certain embodiments, the organic semiconductor of use in the disclosed compositions, methods and apparatus is DAT. Generally, DAT may be produced by reacting 3-amino-L-tyrosine (3AT), with an alkali metal nitrite, such as $NaNO_2$. In preferred embodiments, the 3AT is dissolved first in an aqueous or similar medium before reaction with $NaNO_2$.

Since diazotization reactions are, in general, exothermic, in some embodiments the reaction may be carried out under isothermal conditions or at a reduced temperature, such as, for example, at ice bath temperatures. In certain embodiments, the reaction may be carried out with refluxing for 1 hour, 2 hours, 4 hours, 6 hours or preferably 8 hours, although longer reaction periods of 10, 12, 14, 18, 20 or even 24 hours are contemplated.

The DAT may be precipitated from aqueous solution by addition of a solvent in which DAT is not soluble, such as acetone. After centrifuging the precipitate and discarding the supernatant, the solid material may be dried under vacuum.

In general, the quantities of the 3AT and alkali metal nitrite reactants used are equimolar. It is, however, within the scope of the invention to vary the quantities of the reactants. The molar ratio of 3AT:metal nitrite may be varied over the range of about 0.6:1 to 3:1.

In alternative embodiments, DAT may be partially or fully oxidized prior to use, resulting in the production of oxidized-DAT (O-DAT). Reduced DAT is dissolved in 5 ml of distilled water with 0.2 gm of sodium bicarbonate added. Five milliliters of 30% hydrogen peroxide is added and the mixture is refluxed until the color of the solution changes from brown to yellow. The mixture is cooled, dialyzed against distilled water and lyophilized. The lyophilized powder contains O-DAT.

In certain embodiments, an organic semiconductor such as DAT may be used to neutralize various bioagents, including but not limited to anthrax spores (Kiel et al., 1999a, 1999b). The energy transducing properties of organic semiconductors facilitate the inactivation of bioagents by microwaves, visible light, ultraviolet, infrared or radio-frequency irradiation and/or exposure to pulsed corona discharge (Titan Pulse Sciences Division, San Leandro, Calif.). Although the precise mechanism by which organic semiconductors facilitate bioagent neutralization is unknown, it is possible that the organic semiconductor can absorb various types of energy and convert it to heat, resulting in explosive heating of membrane bound bioagents or in thermal denaturation of non-membrane bound bioagents.

In alternative embodiments, binding moieties that bind to a bioagent with high affinity can be produced to facilitate neutralization of the bioagent. A high affinity binding moiety may be attached to an organic semiconductor, such as DAT. The DAT/binding moiety couplet, after binding to the bioagent, may be activated by a variety of techniques, including exposure to sunlight, heat, plasma (pulsed corona discharge) or irradiation of various types, including laser, microwave, radio-frequency, ultraviolet and infrared. Activation of the DAT/binding moiety couplet results in absorption of energy, which may be transmitted to the bioagent, neutralizing or destroying it.

In other embodiments, organic semiconductors such as DAT may be operably coupled to one or more binding moieties and used to detect a bioagent. In such embodiments, binding of bioagent to the organic semiconductor:binding moiety couplet may result in a change in the electrochemical properties of the couplet that are detectable, for example, as a change in the light emission spectrum of the couplet.

DALM

In certain embodiments, DALM may be used as an organic semiconductor in methods to inactivate bioagents. Production and use of diazoluminomelanin (DALM) has previously been described (Kiel and Parker, 1998; U.S. Pat. Nos. 5,856, 108 and 5,003,050, incorporated herein by reference). DALM is prepared by reacting 3AT (3-amino-L-tyrosine) with an alkali metal nitrite, such as sodium nitrite, and thereafter reacting the resulting diazotized product with luminol. At some point in the reaction, the alaninyl portion of the 3AT rearranges to provide the hydroxyindole portion of the final product. It is believed that such rearrangement occurs following coupling of the luminol to the diazotized 3AT.

The reaction between 3AT and the alkali metal nitrite is carried out in aqueous medium. Since diazotization reactions are, in general, exothermic, it may be desirable to carry out this reaction under isothermal conditions or at a reduced temperature, such as, for example, at ice bath temperatures. The reaction time for the diazotization can range from about 1 to 20 minutes, preferably about 5 to 10 minutes.

Because of the relative insolubility of luminol in aqueous medium, the luminol is dissolved in an aprotic solvent, such as dimethylsulfoxide (DMSO), then added, with stirring, to the aqueous solution of diazotized 3AT. This reaction is carried out, at reduced temperature, for about 20 to 200 minutes. The solvent is then removed by evaporation at low pressure, with moderate heating, e.g., about 30.degree. to 37.degree. C.

The reaction mixture is acidic, having a pH of about 3.5. The coupling of the luminol and the diazotized 3AT can be facilitated by adjusting the pH of the reaction mixture to about 5.0 to 6.0.

The product DALM may be precipitated from the reaction mixture by combining the reaction mixture with an excess of a material that is not a solvent for the DALM, e.g., acetone. After centrifuging the precipitate and discarding the supernatant, the solid material may be dried under vacuum.

In general, the quantities of the 3AT, alkali metal nitrite and luminol reactants are equimolar. It is, however, within the scope of the invention to vary the quantities of the reactants. The molar ratio of 3AT:luminol may be varied over the range of about 0.6:1 to 3:1. DALM is water soluble, having an apparent pKa for solubility about pH 5.0.

In alternative embodiments, DALM may be partially or fully oxidized prior to use, resulting in the production of oxidized-DALM (O-DALM). Reduced DALM is dissolved in 5 ml of distilled water with 0.2 gm of sodium bicarbonate added. Five milliliters of 30% hydrogen peroxide is added and the mixture is refluxed until the color of the solution changes from brown to yellow. The mixture is cooled, dialyzed against distilled water and lyophilized. The lyophilized powder contains O-DALM.

The invention is not limited to the organic semiconductors disclosed in the exemplary embodiments, but may utilize any organic semiconductor that is capable of neutralizing a bioagent.

Attachment of Organic Semiconductors

In various embodiments, organic semiconductors may be attached to other molecules or aggregates, such as binding moieties. Attachment may be accomplished by a variety of binding forces, including but not limited to non-covalent binding, covalent binding, hydrogen bonding, electrostatic forces, hydrophobic interaction, van der Waal forces, or other molecular forces. Attachment may be mediated using a variety of cross-linking agents known in the art, including but not limited to homobifunctional reagents, heterobifunctional reagents, glutaraldehyde, and carbodiimide. Exemplary methods for cross-linking molecule are disclosed in U.S. Pat. Nos. 5,603,872 and 5,401,511, incorporated herein by reference.

In a preferred embodiment, a binding moiety may bind with a high degree of affinity to both the organic semiconductor and the bioagent. High affinity binding may confer specificity on the binding moiety in recognizing and identifying specific bioagents, permitting the organic semiconductor to achieve sufficient proximity to the bioagent to neutralize or destroy it upon activation.

Energy Sources

High Powered Pulse Microwave Irradiation

In certain embodiments, high power pulsed microwave radiation (HPM) applied to solutions containing an organic semiconductor, dissolved carbon dioxide (or bicarbonate), and hydrogen peroxide activates the organic semiconductor by generating sound, pulsed luminescence and electrical discharge. In one embodiment, an organic semiconductor, pulsed with microwave radiation, may act as a photochemical transducer, releasing an intense pulse of visible light and electrical discharge that may neutralize or destroy bioagents such as *Bacillus anthracis* spores. Infectious bioagents exposed to organic semiconductors and pulsed with microwave radiation experience damage comparable to short time, high temperature insults, although measured localized temperatures were insufficient to cause the observed effects.

Pulsed Corona Reactor (PCR) Apparatus

In alternative embodiments, a source of pulsed corona discharge, such as a pulsed corona reactor (PCR) (Titan Pulse Sciences Division, San Leandro, Calif.) may be used to create a non-thermal plasma source. This plasma constitutes a fourth state of matter, possessing anti-microbial activity. The anti-microbial activity of pulsed corona discharge may be enhanced by using organic semiconductors. In some embodiments, the plasma may pass over and onto the surface of PCR sample pins onto which *Bacillus anthracis* spore suspensions are applied.

A PCR apparatus typically comprises two subassemblies—the control cabinet and the pulser/reactor combination. The control cabinet houses the electronic and gas controls required to regulate the high voltage charging power supply as well as the pulse power delivered to the reactor gas. The pulser/reactor assembly contains the pulse power generator and pulsed corona discharge reaction chambers. These two sub-assemblies are connected by a high voltage cable for charging the capacitors in the pulsed power system and by high-pressure gas lines for controlling the voltage delivered to the reactor. Electrical and switch gas supplies are connected to the control cabinet. The reactor gas supply and exhaust lines are connected directly to the reactor. The Titan PCR unit contains test ports with sample pin holders located on two reactor tubes and an exhaust manifold.

EXAMPLES

The following non-limiting examples are included to demonstrate preferred embodiments of the invention. It should be appreciated by those of ordinary skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Neutralization of Anthrax Spores Using Organic Semiconductors and Pulsed Microwave Exposure Organic semiconductors are capable of absorbing electromagnetic radiation within a broad range of wavelengths and transmitting the absorbed energy to bioagents with which they are associated. The activating radiation may be supplied in the form of visible light or infrared radiation, although other forms of energy, such as microwave, laser or radiofrequency irradiation or pulsed corona discharge are contemplated within the scope of the present invention. Irradiation results in absorption of energy by the organic semiconductor and transmission to the bioagent. The resulting heating and production of reactive chemical species produces an explosive surface reaction that neutralizes the bioagent. In preferred embodiments, neutralization is manifested as nonviability or death of the bioagent.

Activation of an exemplary organic semiconductor (DALM) by exposure to hydrogen peroxide and bicarbonate, followed by a pulse of microwave radiation, results in the release of an intense pulse of visible light (not shown). High power pulsed microwave radiation (HPM), applied to solutions containing dissolved carbon dioxide (or bicarbonate), hydrogen peroxide and DALM generates sound, pulsed luminescence and electrical discharge. Microbes exposed to these conditions experience damage comparable to brief, high temperature exposures, even though measurable localized temperatures were apparently insufficient to cause the observed destructive effects.

Materials and Methods

Anthrax Spores—Sterne strain veterinary vaccine *Bacillus anthracis* (hereinafter "BA") spores (Thraxol-2, Mobay Corp., Shawnee, Kans.) were streaked onto blood agar plates and incubated at 37.degree. C. for 5 days to promote extensive growth, with subsequent sporulation and autolysis of vegetative bacterial cells. Colonies were gently washed and scraped from the blood agar plates into 10 ml of filter-sterilized deionized water. The resultant suspension consisted almost exclusively of spores. Most vegetative bacterial cell debris appeared to be removed by three washes in 10 ml of filter-sterilized deionized water with resuspension and centrifugation at 9,300.times.G for 10 min, as determined by phase-contrast microscopy. Stock spore suspension concentration was determined by the average of four hemocytometer chamber field counts to be 6.5.times.10.sup.6 spores/ml (standard deviation=0.24.times.10.sup.6) using phase-contrast microscopy at 600.times. magnification.

*Bacillus anthracis* spores were incubated with DALM and exposed to a high power microwave (HPM) pulse. *Bacillus anthracis* (BA; Sterne strain) spore vaccine (Thraxol™, Mobay Corp., Animal Health Division, Shawnee, Kans. 66201) was centrifuged, the supernatant decanted, and the BA pellet washed with chilled deionized water. Dilute powdered milk solution was made to a concentration of 25 mg of powdered milk solids/ml of deionized water, filtered through a 0.2 micron filter. The BA pellet was resuspended in 1 ml of sterile milk solution to form a BA suspension.

For pulsed microwave exposure, 0.5 ml of BA spore suspension was placed into 0.2 micron-filter centrifuge tubes (Microfilterfuge™, Rainin Instrument Co., Inc., Woburn, Mass. 01888-4026). The spores were centrifuged onto the filter at 16,000.times.g for 15 min. The tubes were refilled with 1.5 ml of a reaction mixture consisting of 0.9 ml saturated sodium bicarbonate/luminol solution, 0.1 ml of 1:10 DALM, 0.6 ml of 1:10 diazoluminol, and 0.33 ml 3% hydrogen peroxide. All dilutions were made in saturated sodium bicarbonate/luminol solution. The final dilution of DALM was 1:1000. A detailed description of the reaction mixture has been published (Kiel et al., 1999a; Kiel et al., 1999b).

The filter, with the BA spores, was inserted into the tube to a level just below the meniscus of the fluid. The solution was exposed to 10 pulses per second of HPM (1.25 GHz, 6.mu.s pulse, 2 MW peak incident power), starting at 3 minutes and 22 seconds after placing the reaction mixture in front of the microwave waveguide. The exposure lasted for 13 min and 28 sec. Total radiation exposure was for 48 msec. The temperature of the sample, continuously monitored with a non-perturbing, high-resistance temperature probe (Vitek™), began at 25.3.degree. C. and reached an end point of 64.degree. C., below the lethal temperature for anthrax spores.

Results

Figures 1A, 1B:
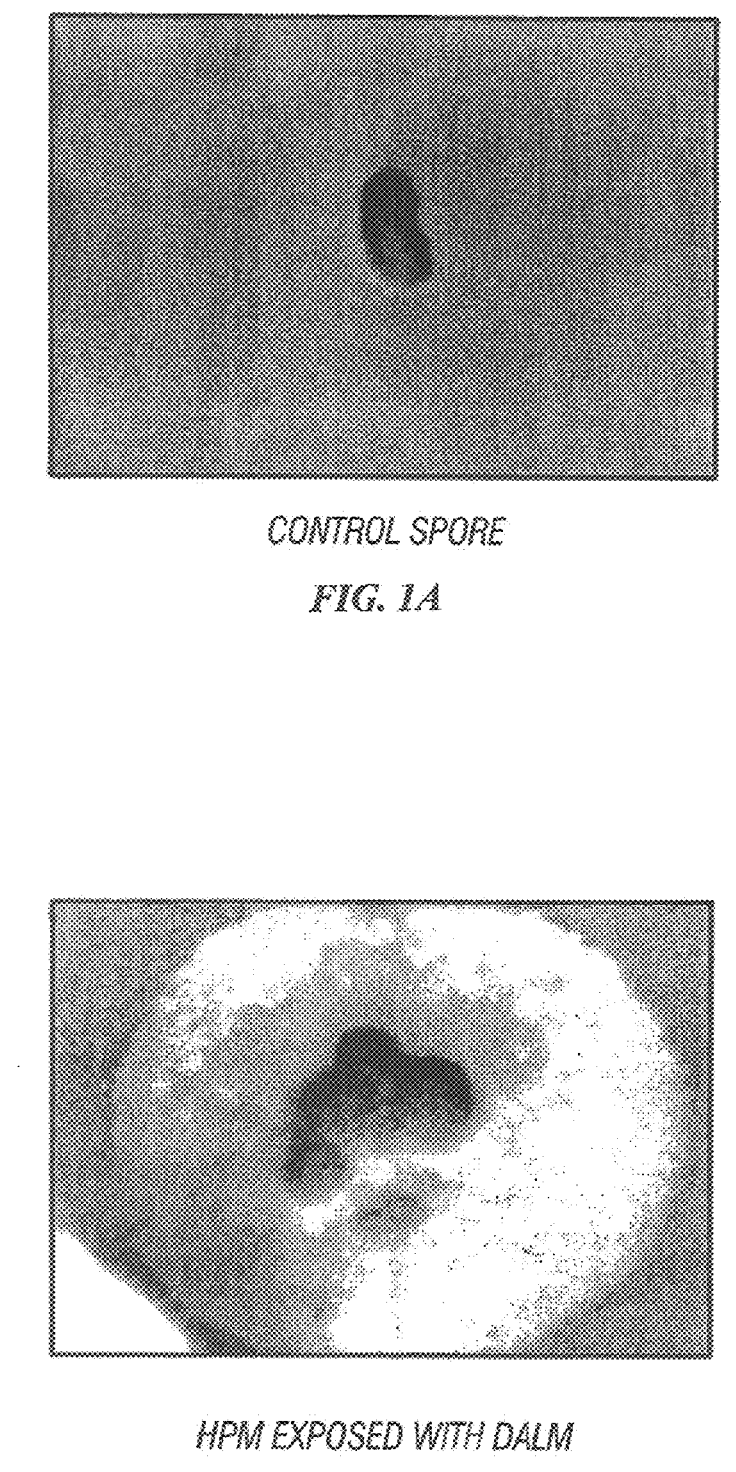

FIGS. 1A-1B shows the result of this procedure. The control spore was exposed to HPM radiation in the absence of DALM. It remained intact (FIG. 1A). The anthrax spore shown in FIG. 1B was exposed to HPM radiation in the presence of DALM. The spore lysed, with its contents visibly distributed around the remnants of the spore casing (FIG. 1B). The effect of the HPM radiation to activate DALM in contact with anthrax spores resulting in spore lysis, shows that activated organic semiconductors such as DALM may be used to neutralize bioagents, such as anthrax spores.

Example 2

Neutralization of Anthrax Spores Using an Organic Semiconductor and Pulsed Corona Reactor Materials & Methods A pulsed corona reactor (PCR) was obtained from Titan Pulse Sciences Division, (San Leandro, Calif.). The high voltage supply in the control cabinet charges the capacitors located inside the pulser sub-assembly. Once the voltage on the capacitors is sufficiently high, a high-pressure spark gap switch located in the pulser wires closes, connecting the capacitors to the reactor wires. The high DC voltage applied to the wires causes gas flowing through the reactor to degrade electrically, creating plasma output. The energy from the capacitors is then discharged very quickly into the plasma. Once all the stored energy is dissipated in the plasma, the discharge stops. Thus, the plasma remains non-thermal.

The electronic and gas controls in the control cabinet regulate the pulse repetition rate and charge voltage, and monitor for faults in the system. The stored energy may be varied by changing the voltage or by adding or removing capacitors from the pulser. The average power delivered to the reactor gas is determined by the energy stored in the capacitors and the repetition rate.

Anthrax Spore Treatment, Sample Application, and PCR Apparatus Exposure-*Bacillus anthracis* spores were exposed to two test conditions. In the first test condition, untreated spores were applied to sample pins of the PCR. In the second test condition, *B. anthracis* spores were pre-incubated in a DALM solution prior to application to the sample pins. Non-intrusive stainless steel sample pins were used, with sample ends fitting flush with the inside wall of the PCR tube. Sample pins coated with identical quantities of either *B. anthracis* spores or *B. anthracis* spores pre-treated with DALM were irradiated simultaneously in the PCR apparatus to ensure uniform exposure conditions. PCR operating parameters were 200 Hz into 5 liters/min air flow for 10 minutes exposure time for the first and second test conditions. Control sample pins coated with identical amounts of *B. anthracis* spores were placed in the PCR apparatus and exposed only to 5 liters/min air flow for 10 min of exposure time, without plasma exposure.

At the end of the exposure, sample pins were immediately removed and placed in separate microtubes containing phosphate buffered saline (PBS). Control and test microtubes were agitated to remove spores from the pin surfaces. Serial dilutions of the spores in control and test tubes in PBS were plated onto tryptic soy agar plates. Colony forming units (CFUs) were counted after incubation. The percentage of kill was calculated as [1−(test CFU/controlCFU)].times.100.

Results

Figure 3:
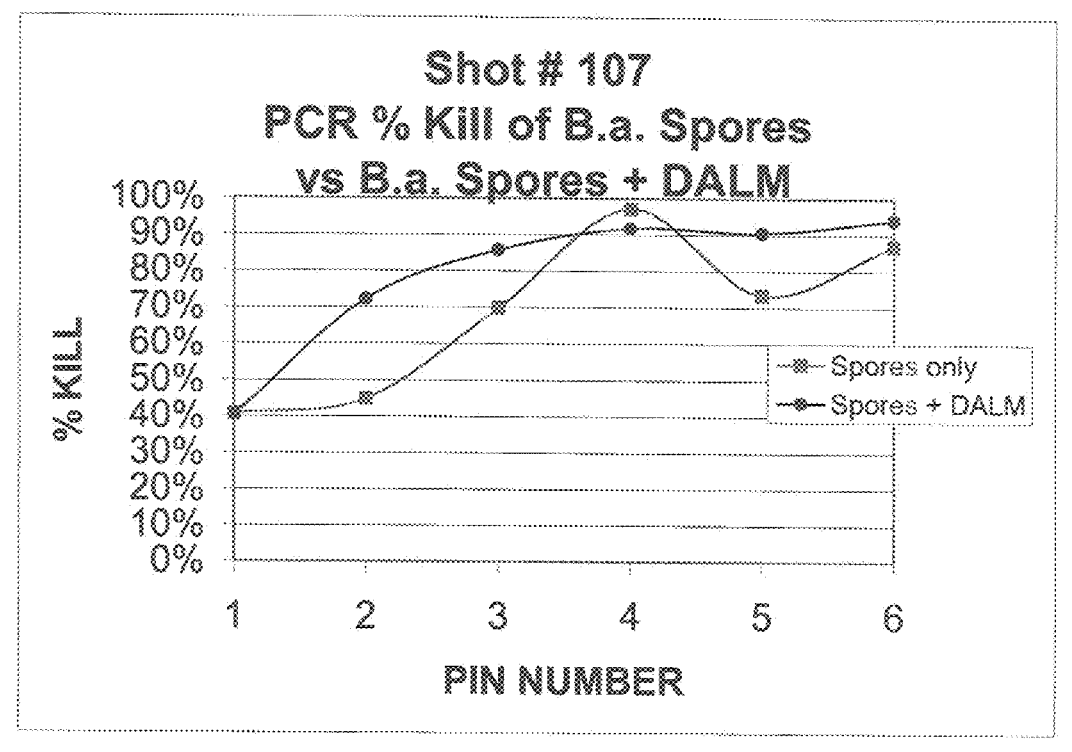

The results of the two test conditions are illustrated for replicate assays conducted as described above (FIG. 2 and FIG. 3). As illustrated in FIG. 2 and FIG. 3, both test conditions resulted in killing of anthrax spores that was close to 100% effective towards the end of the plasma reactor chamber. The pins were located sequentially along the reactor chamber, with pin #1 at the beginning of the reactor chamber and pin #5 at the end of the chamber. Pin #6 is the exhaust pin, where no plasma exists. However, it is evident that reactive species with antimicrobial activity are present in the exhaust. The identity of the antimicrobial species is unknown. However, it is generated by the plasma discharge process, since the control anthrax spores were treated with exhaust in the absence of plasma discharge. It is possible that the anthrax spores are neutralized not by plasma per se, but rather by one or more reactive byproducts of the plasma discharge process.

FIG. 2 and FIG. 3 also show that pre-exposure to an organic semiconductor, such as DALM, potentiates the neutralizing effect of exposure to PCR. Spores pre-incubated with DALM showed consistently higher levels of neutralization than spores in the absence of DALM. These results support the conclusion that use of organic semiconductors in combination with a pulsed corona reactor or other source of activating energy would allow the neutralization of bioagents, such as anthrax, with lower power requirements than neutralization in the absence of an organic semiconductor. The lower power requirements in turn would allow production of compact, portable neutralization apparatus that could be used for field decontamination purposes.

Example 3

Preparation of Binding Moieties Against Anthrax Spores

In certain embodiments, organic semiconductors may be attached to binding moieties that are selective or specific for one or more bioagents to be neutralized. A non-limiting example of a binding moiety within the scope of the invention would be a nucleic acid ligand. Nucleic acid ligands may be selected from random-sequence nucleic acid pools by a process known as SELEX (U.S. Pat. Nos. 5,270,163; 5,475,096; 5,567,588; 5,580,737; 5,595,877; 5,641,629; 5,650,275; 5,683,867; 5,696,249; 5,707,796; 5,763,177; 5,817,785; 5,874,218; 5,958,691; 6,001,577; 6,030,776; each incorporated herein by reference). The SELEX methodology was used to develop high affinity single stranded DNA (ssDNA) ligands that bind to anthrax spores.

Libraries and Primers: The starting material for SELEX preparation of anti-anthrax nucleic acid ligands comprised synthetic DNA containing fixed sequences for primer annealing in a PCR amplification reaction. The starting nucleic acid ligand library was composed of 86-mers, containing 40-mer random DNA sequences (N40) attached to 5' and 3' fixed primer annealing sequences, as shown in Table 2 below.

TABLE 2

| 5' Fixed sequences for primer annealing | Random sequences | 3' Fixed sequences for primer annealing |
|---|---|---|
| 5'-CCCCTGCAGGTGATTT T GCTCAAGT-3' (SEQ ID NO: 1) | NNNN--- NNNN (40N) | 5'-AGTATCGCTAAT CA GGCGGAT-3' (SEQ ID NO: 2) |

In the Table above, N represents an equal mixture of all four nucleotides (A, G, T and C). The 5' end of the 5' fixed sequence was covalently attached to three biotin residues to facilitate binding of the nucleic acid ligands to streptavidin. The oligonucleotide library and corresponding PCR primers were purchased from Genosys (The Woodland, Tex.). Taq polymerase was obtained from Display Systems Biotech (Vista, Calif.). A dNTP mixture was purchased from Applied Biosystems (Foster City, Calif.). Ultra pure urea, bis-acrylamide, fluor-coated TLC plates and buffer saturated phenol were from Ambion (Austin, Tex.). Glycogen and streptavidin-linked beads were purchased from Roche Molecular Biochemicals (Indianapolis, Ind.). Spin columns and 10.times.TBE (Tris-borate-EDTA) buffer were from BioRad (Hercules, Calif.). Nitrocellulose discs were from Millipore (Bedford, Mass.). All other reagent grade chemicals were purchased from Sigma (St. Louis, Mo.). Anthrax Spore Vaccine, a non-encapsulated live culture, was supplied by the Colorado Serum Company (Denver, Colo.).

Anthrax Spores: Anthrax spore vaccine was transferred from the manufacturer's vial to sterile centrifugation tubes that had been chilled on ice. The spores were pelleted by centrifuging at 9500.times.g for 10 min at 4.degree. C. and the pellet was washed with ice cold sterile distilled water. Spores were resuspended in ice cold, sterile distilled water and stored temporarily at 4.degree. C.

AK sporulation agar was used to make agar plates according to the manufacturer's instructions. Sterile cotton-tipped swabs were used to streak each agar plate with the anthrax spore suspension. Plates were incubated at 37.degree. C. for 4 days and then checked for complete sporulation under a light microscope. Spores were harvested from the plates by using sterile cotton tipped swabs wetted with distilled water. The swab was run across the plate and placed into sterile ice-cold distilled water. The entire layer of anthrax growth was removed and transferred to distilled water. The spore suspension was then vacuum filtered using a sterile Buchner funnel and Whatman filter paper into a sterile flask in an ice bath. The spores are filtered through the filter paper while vegetative debris is trapped on the filter paper. The filtrate consisted almost entirely of spores. The spores were heat treated at 65.degree. C. for 30 min and cooled immediately in an ice bath. The suspension was centrifuged at 9500.times.g for 10 min, resuspended in ice cold sterile distilled water and stored at 4.degree. C. until use. Stock spore suspension concentration was determined from the average colony forming units (CFUs) obtained from triple replicates at five different dilutions of stock suspension.

The initial nucleic acid ligand library was amplified by PCR. The 5' primer used was identical to SEQ ID NO:1, disclosed above, with 3 biotin residues attached to the 5' end of the primer. The 3' primer was complementary to the 3' fixed sequence disclosed in Table 2 and is shown below as SEQ ID NO:3. PCR conditions were checked in 200.mu.L reaction mixture, using 5 pmol of template and 0.1.mu.M of each primer, 20.mu.L of 10.times.PCR reaction buffer, 2.mu.L of 10 mM dNTP mix and 5 units of display TAQ polymerase, with distilled water added to 200.mu.L. Optimal PCR conditions were determined to be denaturation at 94.degree. C. for 3 min, annealing at 45.degree. C. for 30 sec, and extension at 72.degree. C. for 1 min, with a final extension at 72.degree. C. for 3 min. The reaction was performed using a Robocycler Model 96 thermal cycler with a "Hot Top" assembly (Stratagene, La Jolla, Calif.). The PCR product was checked every third cycle and the optimal number of cycles determined. After obtaining optimal conditions, the original library was amplified to prepare 25 ml of reaction mix (125 reactions at 200.mu.L each). The amplified DNA pool was recovered by ethanol precipitation in the presence of glycogen and the final DNA pellet was resuspended in sterile TE buffer [Tris-HCl, EDTA, pH 8.0] and used for streptavidin binding.

(SEQ ID NO: 3)
5'-ATCCGCCTGATTAGCGATACT-3'

Streptavidin Binding: Resuspended double stranded DNA was mixed with streptavidin agarose beads and incubated at room temperature to allow binding of biotin labeled DNA to streptavidin. The mixture was transferred to spin columns and denatured by addition of 0.2 M NaOH. The biotin labeled DNA strand remained in the column along with the streptavidin beads, while the unlabeled strand passed through the column and was collected. The eluate was neutralized with 3 M sodium acetate, pH 5.0, ethanol precipitated overnight and recovered by centrifugation at 4.degree. C. at 13,000 rpm. The ssDNA pellet was resuspended in TE buffer and used for gel purification.

Gel Purification of ssDNA: The ssDNA was mixed with a denaturing 2.times. sample buffer containing 90% formamide, 1 mM EDTA and 0.1% bromophenol blue and heated at 90.degree. C. for 5 min. After cooling to room temperature, the contents were separated by electrophoresis in a 6% acrylamide/bis (19:1) gel, with 7M urea in 1.times.TBE buffer for 2 hours at 150 volts. The ssDNA was visualized under UV light and the bands cut out and eluted overnight in 0.3 M sodium chloride. Eluted DNA was ethanol precipitated overnight and collected by centrifugation. The DNA pellet was resuspended in TE buffer and used for in vitro selection.

In vitro Selection by SELEX: To exclude filter-binding ssDNA sequences from the pool, the DNA was initially passed over a 0.45.mu.m HAWP filter (Millipore, Bedford, Mass.) and washed with TE buffer. The filtrate containing non-binding DNA was used for in vitro selection. In general, the final yield of ssDNA was in the .mu.mole range. One hundred pmol of ssDNA was incubated with live anthrax spores (0.5.times.10.sup.6 spores) in binding buffer (20 mM Tris-HCl, pH 7.5, 45 mM sodium chloride, 3 mM magnesium chloride, 1 mM EDTA, 1 mM diothiothreitol in a final volume of 250.mu.L) (Hesselberth et al., 2000). The binding reaction mixture was incubated for one hour at room temperature, then vacuum filtered through a HAWP filter at 5 psi and washed twice with 0.2 ml of binding buffer. DNA that bound to anthrax spores was retained on the filter, while nucleic acid ligands that did not bind to anthrax passed through the filter. The anthrax-binding ssDNA was eluted 2× with 0.2 ml of 7 M urea, 100 mM MES (4-morpholine-ethansulfonic acid, Roche Molecular Biochemicals), pH 5.5, 3 mM EDTA for 5 min at 100.degree. C. The eluted anthrax-binding ssDNA was ethanol precipitated overnight and collected by centrifugation. The pelleted DNA was resuspended and used for the next round of SELEX selection.

Results: The methods described above resulted in the production of ssDNA nucleic acid ligands that bind with high affinity to live anthrax spores (*Bacillus anthracis* Sterne strain). In vitro selection was performed using the SELEX procedure as described above. Nucleic acid ligands containing 40 by random DNA sequences were screened for binding to live anthrax spores. Anthrax-binding nucleic acid ligands were eluted, amplified by PCR and subjected to further rounds of SELEX screening. A total of seven rounds of SELEX screening were performed. Gel electrophoresis analysis showed that the PCR amplification products after each round were the same size (86-mer) as the original pool, demonstrating that the primers were amplifying nucleic acid ligand sequences, not anthrax genomic sequences. Controls performed in the absence of anthrax spores, or in the presence of spores but the absence of the ssDNA pool, showed no PCR amplification product, demonstrating that the SELEX procedure resulted in the production of anthrax-binding nucleic acid ligands (not shown).

After five rounds of SELEX selection, the amplification product was present as essentially a single band (not shown). The anthrax-binding amplification product was the same size as the PCR amplification products of the initial random nucleic acid library (not shown). A zero amplification control showed that the band was not observed in the absence of amplification (not shown). The nucleic acid ligand bound to anthrax spores with high selectivity and affinity (not shown).

The sequences of anthrax-binding nucleic acid ligands identified by the disclosed methods were as shown below.

3

SEQ ID NO: 4
5'-GGATGAAATTATGAAGGAGTAATAGTGTGATGGAGTGGTA-- 3'

SEQ ID NO: 5
5'-ACCCGGTTAATTCGTAGTAGAGGAGGGTC- GTTTGGAGTCA-3'

SEQ ID NO: 6
5'-AGAGGAATGTATAAGGATGTTCCGGGCGTGTGGGTAAGTC-3'

Example 4

Synthesis of DAT

Another exemplary organic semiconductor of use in the practice of the invention is DAT. To produce DAT, 3-amino-L-tyrosine (3AT) (1.776 gm) was dissolved in 50 ml of distilled water. Then $NaNO_2$ (0.417 gm) was added to the solution. After 4 min, the mixture of 3AT and sodium nitrite was subjected to refluxing for approximately 8 hours. The resulting DAT was precipitated by addition of acetone and the precipitate was allowed to sit overnight in a separatory funnel.

DAT was collected from solution by centrifugation at 3,000 rpm for 10 min. DAT was resuspended in distilled water and dialyzed against distilled water in a 3,500 Dalton molecular weight cutoff bag.

The spectroscopic properties of DAT were similar to those of DALM in a NaBr solvent system (not shown). Under these conditions DALM exhibited an excitation peak at 365 nm and an emission peak at 450 nm, while DAT exhibited and excitation peak at 387 nm and an emission peak at 447 nm.

Example 5

Neutralizing Anthrax Spores with DALM and DAT

Materials and Methods

Anthrax spores preincubated with organic semiconductors were exposed to microwave radiation as disclosed in Example 1, with the following modifications. Anthrax spores pre-treated with organic semiconductor were applied to No. 3 Whatman filters contained in snap-lid petri dishes. The dishes were arranged in a nine plate array. Dishes were centered vertically and horizontally in front of a 2.06 GHz L-band microwave transmitter and exposed to microwave radiation at 400 W, 10 Hz with 10 msec pulses for 15 min exposure time. After microwave exposure, filter papers were vigorously vortexed in buffer and aliquots were plated to determine colony forming units (CFU). Percent kill was determined as in Example 2.

The efficacy of DALM and DAT in promoting microwave induced killing of anthrax spores was examined. In some cases, purified DALM or DAT were treated with hydrogen peroxide to produce oxidized forms of DALM (O-DALM) or DAT (O-DAT).

Results

DALM and DAT showed approximately equal efficacy at promoting microwave mediated destruction of anthrax spores. However, the oxidized forms (O-DALM and O-DAT) were more efficient at inducing anthrax spore destruction than the unoxidized forms. Percent kill observed was 67.5% for O-DALM and 45.7% for O-DAT. Under the conditions of this study, pretreatment with unoxidized DALM and DAT did not result in detectable destruction of anthrax spores.

These results show that DAT exhibits similar properties to DALM in mediating energy dependent destruction of anthrax spores and that oxidation with hydrogen peroxide or similar agents may increased the efficacy of organic semiconductors in neutralizing bioagents.

All of the COMPOSITIONS, METHODS and APPARATUS disclosed and claimed herein can be made and executed without undue experimentation in light of the present disclosure. While the compositions and methods of this invention have been described in terms of preferred embodiments, it will be apparent to those of skill in the art that variations may be applied to the COMPOSITIONS, METHODS and APPARATUS and in the steps or in the sequence of steps of the methods described herein without departing from the concept, spirit and scope of the invention. All such similar substitutes and modifications apparent to those skilled in the art are deemed to be within the spirit, scope and concept of the invention as defined by the appended claims.

Reference

The following references, to the extent that they provide exemplary procedural or other details supplementary to those set forth herein, are specifically incorporated herein by reference.

Bruno and Yu, Immunomagnetic-electrochemiluminescent detection of *Bacillus anthracis* spores in soil matrices. Appl. Environ. Microbiol. 62: 3474-76, 1996.

Bruno et al., Preliminary electrochemiluminescence studies of metal ion-bacterial diazoluminomelanin (DALM) interactions. J. Biolumin. Chemilumin. 13: 117-123, 1998.

Gatto-Menking et al., Sensitive detection of biotoxoids and bacterial spores using an immunomagnetic electrochemiluminescence sensor. Biosensors Bioelectronics 10: 501-507, 1995.

Hesselberth et al., In vitro selection of RNA molecules that inhibit the activity of the ricin A-chain. J. Biol. Chem. 275: 4937-42, 2000.

Kiel and Parker, Enhanced Nitrate Production and Diazoluminomelanin Synthesis in Mouse Mammary Tumor Cells Transfected with a Plant Nitrate Reductase Gene Fragment, In Vitro Cell. Dev. Bio. Animal 34: 734-739 (1998).

Kiel et al. "Luminescent radio frequency radiation dosimetry." Bioelectromagnetics 20:46-51, 1999a.

Kiel et al., "Pulsed microwave induced light, sound, and electrical discharge enhanced by a biopolymer." Bioelectromagnetics 20:216-223, 1999b.

Kiel et al. "Rapid recovery and identification of anthrax bacteria from the environment." N.Y. Acad. Sci. 916:240-252, 2000.

Reif et al., Identification of capsule-forming *Bacillus anthracis* spores with the PCR and a novel dual-probe hybridization format. Appl. Environ. Microbiol. 60:1622-25, 1994.

U.S. Pat. No. 5,003,050
U.S. Pat. No. 5,270,163
U.S. Pat. No. 5,401,511
U.S. Pat. No. 5,475,096
U.S. Pat. No. 5,567,588
U.S. Pat. No. 5,580,737
U.S. Pat. No. 5,595,877
U.S. Pat. No. 5,603,872
U.S. Pat. No. 5,641,629
U.S. Pat. No. 5,650,275
U.S. Pat. No. 5,683,867
U.S. Pat. No. 5,696,249
U.S. Pat. No. 5,707,796
U.S. Pat. No. 5,763,177
U.S. Pat. No. 5,817,785
U.S. Pat. No. 5,856,108
U.S. Pat. No. 5,874,218
U.S. Pat. No. 5,958,691
U.S. Pat. No. 6,001,577
U.S. Pat. No. 6,030,776
U.S. Pat. No. 6,303,316

What is claimed:

1. A decontamination method for neutralizing *Bacillus anthracis* or *Bacillus anthracis* spores comprising:
    a) exposing *Bacillus anthracis* or *Bacillus anthracis* spores to an organic semiconductor attached to one or more nucleic acid ligands capable of associating with *Bacillus anthracis* or *Bacillus anthracis* spores, the organic semiconductor having a conjugated backbone of alternating double and single bonds and is capable of transporting positive and negative charges; and
    b) neutralizing the *Bacillus anthracis* or *Bacillus anthracis* spores by irradiating the *Bacillus anthracis* or *Bacillus anthracis* spores exposed to the organic semiconductor attached to the nucleic acid ligands with an energy source selected from the group consisting of radiofrequency radiation, microwave, electron beam radiation, and non-thermal plasma discharge,
    wherein neutralization is increased compared to irradiating the *Bacillus anthracis* or *Bacillus anthracis* spores exposed to an organic semiconductor without an attached nucleic acid ligand.

2. The method of claim 1, wherein the organic semiconductor is selected from the group consisting of polydiazotyrosine (DAT) and diazoluminomelanin (DALM).

3. The method of claim 1, wherein the organic semiconductor is oxidized.

4. The method of claim 1, wherein the source of energy is non-thermal plasma discharge.

5. The method of claim 1, wherein the nucleic acid ligands bind to the *Bacillus anthracis* spores.

6. The method of claim 1, further comprising neutralizing the *Bacillus anthracis* or *Bacillus anthracis* spores on a solid surface, wherein neutralizing the *Bacillus anthracis* or *Bacillus anthracis* spores on the solid surface comprises destroying or killing the *Bacillus anthracis* or *Bacillus anthracis* spores.

7. The method of claim 6, wherein the solid surface comprises metal, paper or a combination thereof.

8. The method of claim 1, wherein the organic semiconductor is half oxidized and half reduced.

9. The method of claim 1, wherein the nucleic acid ligands capable of associating with *Bacillus anthracis* or *Bacillus anthracis* spores were obtained using SELEX™.

10. A decontamination method for neutralizing *Bacillus anthracis* or *Bacillus anthracis* spores associated with a solid surface comprising:
  a) exposing the *Bacillus anthracis* or *Bacillus anthracis* spores on the solid surface to an organic semiconductor attached to one or more nucleic acid ligands of 5 or more consecutive nucleotides in length capable of associating with *Bacillus anthracis* or *Bacillus anthracis* spores; and
  b) neutralizing the *Bacillus anthracis* or *Bacillus anthracis* spores on the solid surface by irradiating the *Bacillus anthracis* or *Bacillus anthracis* spores exposed to the organic semiconductor attached to the one or more nucleic acid ligands with an energy source selected from the group consisting of radio frequency radiation, microwave, electron beam radiation, and non-thermal plasma discharge,
  wherein neutralization is increased compared to irradiating the *Bacillus anthracis* or *Bacillus anthracis* spores exposed to an organic semiconductor without an attached nucleic acid-ligand.

11. The method of claim 10, wherein the organic semiconductor is selected from the group consisting of polydiazoaminotyrosine (DAT) and diazoluminomelanin (DALM).

12. The method of claim 10, wherein the source of energy is high power pulsed microwave radiation.

13. The method of claim 10, wherein the source of energy is non-thermal plasma discharge.

14. The method of claim 10, wherein the nucleic acid ligands capable of associating with *Bacillus anthracis* or *Bacillus anthracis* spores were obtained using SELEX™.

* * * * *

SEQUENCE LISTING

```
<160> NUMBER OF SEQ ID NOS: 6

<210> SEQ ID NO 1
<211> LENGTH: 25
<212> TYPE: DNA
<213> ORGANISM: Artificial Sequence
<220> FEATURE:
<223> OTHER INFORMATION: oligonucleotide

<400> SEQUENCE: 1
cccctgcagg tgatttgct caagt                                          25

<210> SEQ ID NO 2
<211> LENGTH: 21
<212> TYPE: DNA
<213> ORGANISM: Artificial Sequence
<220> FEATURE:
<223> OTHER INFORMATION: oligonucleotide
```

```
<400> SEQUENCE: 2
agtatcgcta atcaggcgga t                                            21

<210> SEQ ID NO 3
<211> LENGTH: 21
<212> TYPE: DNA
<213> ORGANISM: Artificial Sequence
<220> FEATURE:
<223> OTHER INFORMATION: oligonucleotide

<400> SEQUENCE: 3
atccgcctga ttagcgatac t                                            21

<210> SEQ ID NO 4
<211> LENGTH: 40
<212> TYPE: DNA
<213> ORGANISM: Artificial Sequence
<220> FEATURE:
<223> OTHER INFORMATION: oligonucleotide

<400> SEQUENCE: 4
ggatgaaatt atgaaggagt aatagtgtga tggagtggta                        40

<210> SEQ ID NO 5
<211> LENGTH: 40
<212> TYPE: DNA
<213> ORGANISM: Artificial Sequence
<220> FEATURE:
<223> OTHER INFORMATION: oligonucleotide

<400> SEQUENCE: 5
acccggttaa ttcgtagtag aggagggtcg tttggagtca                        40

<210> SEQ ID NO 6
<211> LENGTH: 40
<212> TYPE: DNA
<213> ORGANISM: Artificial Sequence
<220> FEATURE:
<223> OTHER INFORMATION: oligonucleotide

<400> SEQUENCE: 6
agaggaatgt ataaggatgt tccgggcgtg tgggtaagtc                        40
```